United States Patent [19]

Mizui et al.

[11] Patent Number: 4,997,586
[45] Date of Patent: Mar. 5, 1991

[54] MEDIUM FOR TRANSMITTING MOTIVE POWER

[75] Inventors: Kinya Mizui, Chiba; Harumi Furuta, Iwakuni, both of Japan

[73] Assignee: Mitsui Petrochemical Industries, Ltd., Tokyo, Japan

[21] Appl. No.: 214,052

[22] Filed: Jun. 30, 1988

[51] Int. Cl.$^5$ ............... C09K 5/00; C10M 105/02
[52] U.S. Cl. ............................................. 252/73
[58] Field of Search ............... 585/26, 24, 22; 252/73

[56] References Cited

U.S. PATENT DOCUMENTS 4,570,024  2/1986  Mizui et al. .................... 585/24

OTHER PUBLICATIONS

Smalkeer and Smith, Lubricant Additives, 1967, pp. 1-11.

Primary Examiner—Olik Chaudhuri
Assistant Examiner—Jerry D. Johnson
Attorney, Agent, or Firm—Sherman and Shalloway

[57] ABSTRACT

A medium for transmitting a motive power, comprising a hydrogenated product of an aromatic hydrocarbon compound substituted, for at least one hydrogen atom on an aromatic nucleus, with a tricyclo[5.2.1.0$^{2,6}$]deca-3-yl or tricyclo[5.2.1.0$^{2,6}$]deca-4-yl group which is unsubstituted or substituted with one or more lower alkyl group.

5 Claims, 1 Drawing Sheet

MEDIUM FOR TRANSMITTING MOTIVE POWER

BACKGROUND OF THE INVENTION

1. Field of the Invention

The present invention relates to a medium for transmitting a motive power, hereinafter, motive power transmitting medium, comprising a hydrogenated product of a substituted aromatic hydrocarbon compound. More particularly, the present invention relates to a motive power transmitting medium comprising a hydrogenated product of an aromatic hydrocarbon compound substituted for a hydrogen atom on an aromatic nucleus with a tricyclodecayl group.

2. Description of the Related Art

After conducting various research projects into derivatives from aromatic hydrocarbon compounds and tricyclo[5.2.1.0$^{2,6}$]deca-3-enes, the inventors of the present invention found that a hydrogenated product prepared by reacting a tricyclo[5.2.1.0$^{2,6}$]deca-3-ene and an aromatic hydrocarbon compound and hydrogenating the reaction product is very useful as a motive power transmitting medium.

SUMMARY OF THE INVENTION

The object of the present invention is to provide a motive power transmitting medium comprising a hydrogenated product of a substituted aromatic hydrocarbon compound.

Other objects and advantages of the present invention will be apparent from the following description.

In accordance to the present invention, there is provided a motive power transmitting medium, comprising a hydrogenated product of an aromatic hydrocarbon compound substituted, for at least one hydrogen atom on an aromatic nucleus, with a tricyclo[5.2.1.0$^{2,6}$]deca-3-yl or tricyclo[5.2.1.0$^{2,6}$]deca-4-yl group which is unsubstituted or substituted with one or more lower alkyl group.

BRIEF EXPLANATION OF THE DRAWINGS

In FIGS. 1 and 2, the numbers on the abscissa indicate wave numbers.

DESCRIPTION OF THE PREFERRED EMBODIMENTS

Figure 1:
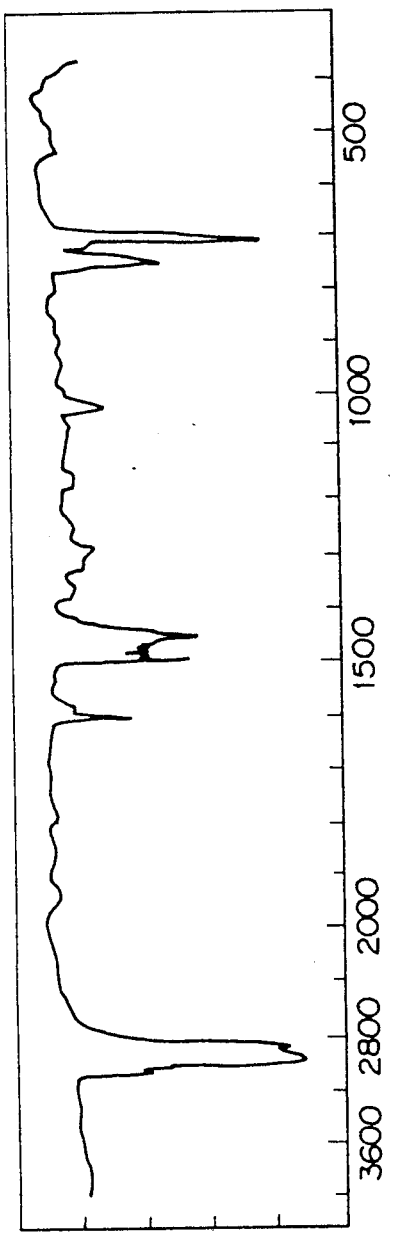
FIGS. 1 and 2 are infrared absorption spectra of reaction products obtained in Examples 1 and 2, respectively.

The tricyclo[5.2.1.0$^{2,6}$]deca-3-yl and tricyclo[5.2.1.0$^{2,6}$]deca-4-yl groups typically have structures of the following formulae (I) and (II), respectively:

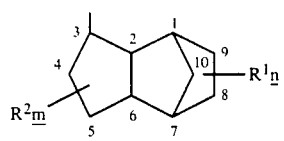

(I)

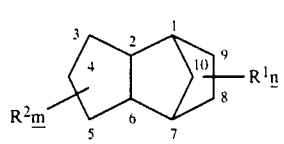

(II)

wherein R$^1$ represents a lower alkyl group at the 1 or 7 to 10 position, and two or more R$^1$'s may be identical to or different from each other, R2 represents a lower alkyl group at the 2–6 position, and two or more R$^2$'s may be identical to or different from each other, n is 0 to 5 and m is 0 to 5. The term "lower" used herein with regard to an alkyl group or the like means that the alkyl group or the like has 1 to 4 carbon atoms.

Starting Materials

An aromatic hydrocarbon compound which may be used as a starting material for the hydrogenated products of the substituted aromatic hydrocarbon compound used in the present invention is, for example, a compound having 6 to 18 carbon atoms, preferably 6 to 14, more preferably 6 to 9, carbon atoms. The aromatic hydrocarbon compound may carry one or more saturated substituent. As examples of the aromatic hydrocarbon compound, there may be mentioned benzene, naphthalene, anthracene or alkyl-substituted derivatives thereof such as toluene, o-xylene, m-ethyltoluene, p-ethyltoluene, n-butylbenzene, isobutylbenzene, sec-butylbenzene, t-butylbenzene, various diethylbenzenes, 1-methylnaphthalene, 2-methylnaphthalene, 9-methylanthracene, or the like. Further, other aromatic hydrocarbon compounds such as biphenyl, terphenyl, indan or the like also may be used. Of the above aromatic hydrocarbon compounds, benzene and mono- or di-alkyl substituted benzene are preferable, but toluene, ethylbenzene, and xylene are particularly preferable.

The other starting material which is reacted with at least one aromatic hydrocarbon compound as mentioned above is a tricyclo[5.2.1.0$^{2,6}$]deca-3-ene having the formula (III):

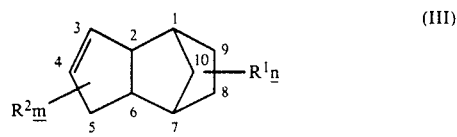

(III)

wherein R$^1$, R$^2$, m and n have the same meanings as given above. Preferably an unsubstituted tricyclo[5.2.1.0$^{2,6}$]deca-3-ene is used, but tricyclo[5.2.1.0$^{2,6}$]deca-3-ene substituted at the 1 or 7–10 position, or at the 2 to 6 position with at least one lower alkyl group such as methyl, ethyl, propyl, iso-propyl, butyl or the like, also may be used. For example, there may be mentioned a 3, 4, 5, 7, 8, 9 or 10-mono-substituted compound, or 5,7-, 5,8-, 5,9-, 5,10-, 4,7-, 4,8-, 4,9-, 3,8-, 3,9-, or 1,4- disubstituted compound.

The above-mentioned tricyclo[5.2.1.0$^{2,6}$]deca-3-enes can be prepared by selectively hydrogenating dicyclopentadienes, as mentioned in Japanese Examined Patent Publication No.47-11818. For the purpose of the present invention, pure tricyclo[5.2.1.0$^{2,6}$]deca-3-enes are preferable, but those having a purity of at least 60% by weight may be used. Further, tricyclo[5.2.1.0$^{2,6}$]deca-3-enes may contain a polymerizable component such as a cyclopentene, tricyclo[5.2.1.0$^{2,6}$]deca-8-ene or a partially hydrogenated product of cyclopentadiene oligomer (at least dimer), or a nonpolymerizable component such as tricyclo[5.2.1.0$^{2,6}$]decane or a derivative thereof.

Preparation of Substituted Aromatic Hydrocarbon Compounds

The aromatic hydrocarbon compound is reacted with about 1-times, preferably about 1.2–10 times, the molar quantity of the tricyclo[5.2.1.0$^{2,6}$]deca-3-ene, optionally in the presence of a reaction solvent, for example, aliphatic hydrocarbon such as pentane, hexane, or heptane, alicyclic hydrocarbon, or halogenated hydrocarbon such as dichloromethane, ethyl chloride, 1,2-dichloroethane, or chlorobenzene, using a Friedel-Craft catalyst. As the reaction solvent, the compound having 5-10 carbon atoms is particularly preferable.

As the Friedel-Craft catalyst, there may be used, for example, a Lewis acid such as $AlCl_3$, $AlBr_3$, $BF_3$, $SnCl_4$, $SnBr_4$, $FeCl_3$, $BeCl_2$, $CdCl_2$, $ZnCl_2$, $BEl_3$, $BBr_3$, $TiCl_4$, $TiBr_4$, $ZrCl_4$ or alkylaluminium dichloride, or a Lewis acid complex such as a complex between $BF_3$ and alcohol, phenol or ether, or a ternary complex of $AlCl_3$, aromatic hydrocarbon compound and hydrogen halide. Preferably, $BF_3$, $AlCl_3$, or a complex thereof is used. The amount of catalyst used varies with the kind of catalyst used, the kind and purity of both starting materials, and the reaction temperature or the like. In general, the catalyst is used at an amount of about 1-50 mole% with respect to the starting aromatic hydrocarbon compound.

The reaction is carried out at a temperature of, generally, about $-10°$ to $200°$ C., preferably about $0°$ to $150°$ C., at atmospheric or an elevated pressure, for about 1 to 10 hours, under the following procedure: Both starting materials, and optionally, the reaction solvent are maintained at a given temperature under a given pressure. Then the catalyst is added, while stirring, and thus the reaction is commenced. After carrying out the reaction for a given period of time, residual catalyst is removed by a conventional method, and unreacted components and the reaction solvent are removed by distillation to obtain the desired substituted aromatic hydrocarbon compound. Here, because little polymerization of the tricyclo[5.2.1.0$^{2,6}$]deca-3-ene used as the starting material has occurred, the desired substituted aromatic hydrocarbon compound is obtained with a relatively high purity.

Preparation of Hydrogenated Product of Substituted Aromatic Hydrocarbon Compound The hydrogenated product of the substituted aromatic hydrocarbon compound used in the present invention may be prepared by hydrogenating the aromatic nucleus included in the above-mentioned substituted aromatic hydrocarbon compound. The hydrogenation is carried out in the presence of an appropriate hydrogenating catalyst, using a solvent. As examples of the catalyst, there may be mentioned a metal belonging to Groups VI and VII of the Periodic Table, or a compound thereof, such as nickel, chromium, palladium, platinum, cobalt, osmium, rhenium, ruthenium, Raney nickel, nickel sulfide, nickel oxide, copper chromite, cobalt-molybdate, molybdenum sulfide, platinum oxide, cobalt oxide, rhenium oxide, ruthenium oxide, sponge iron, iron oxide or the like. Various solvents may be used. For example, an aliphatic or alicyclic solvent such as pentane, hexane, heptane, isoheptane, octane, isooctane, cyclohexane, methylcyclohexane, decalin may be used.

If the substituted aromatic hydrocarbon compound as the starting material is a liquid having a low viscosity at a given reaction temperature, the hydrogenation can be performed without a solvent.

The hydrogenation is carried out batchwise or continuously, at a temperature of, usually, $20°$ to $300°$ C., preferably about $100°$ to $240°$ C., under a reduced or elevated pressure, generally from atmospheric pressure to about 300 kg/cm$^2$G, preferably about 10-150 kg/cm$^2$G, for about 10 minutes to about 24 hours, preferably about 10 minutes to about 7 hours, by means of a treatment with hydrogen gas.

After the hydrogenation is finished, the solvent, the unhydrogenated substituted aromatic hydrocarbon compound, and the hydrogenated substituted aromatic hydrocarbon compound can be separated from each other by a conventional method such as distillation. But, if the hydrogenated product of the substituted aromatic hydrocarbon compound is used as an additive for an adhesive, it is not necessary to remove the unhydrogenated substituted aromatic hydrocarbon compound, because both can be used in the form of a mixture thereof. In this case, the ratio of hydrogenation for the whole mixture is preferably 10% or more, particularly 40% or more.

Hydrogenated Product

The resulting hydrogenated product of the substituted aromatic hydrocarbon compound preferably has the structure of, for example, the following formula (IV):

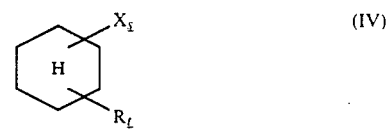

wherein X represents tricyclo[5.2.1.0$^{2,6}$]deca-3-yl or tricyclo[5.2.1.0$^{2,6}$]deca-4-yl group which may be substituted with one or more lower alkyl group, R represents a lower alkyl group, t is an integer of 1 or 2, and s is an integer of 1 to 3, with the proviso that if s is 2 or 3, two or three X's are in meta-position to each other.

Typical hydrogenated products of the formula (IV) are shown as follows:

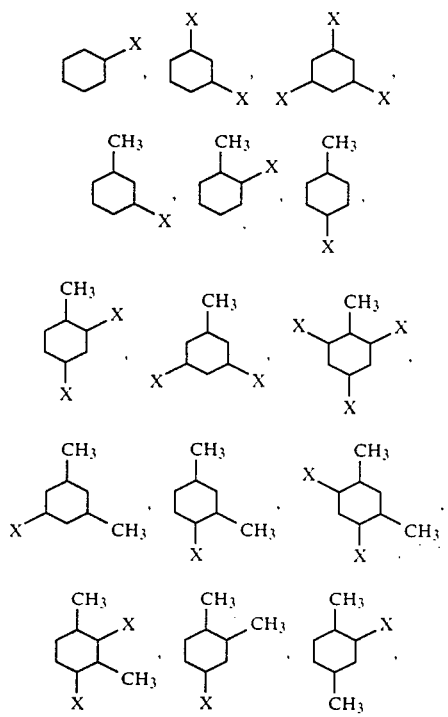

-continued

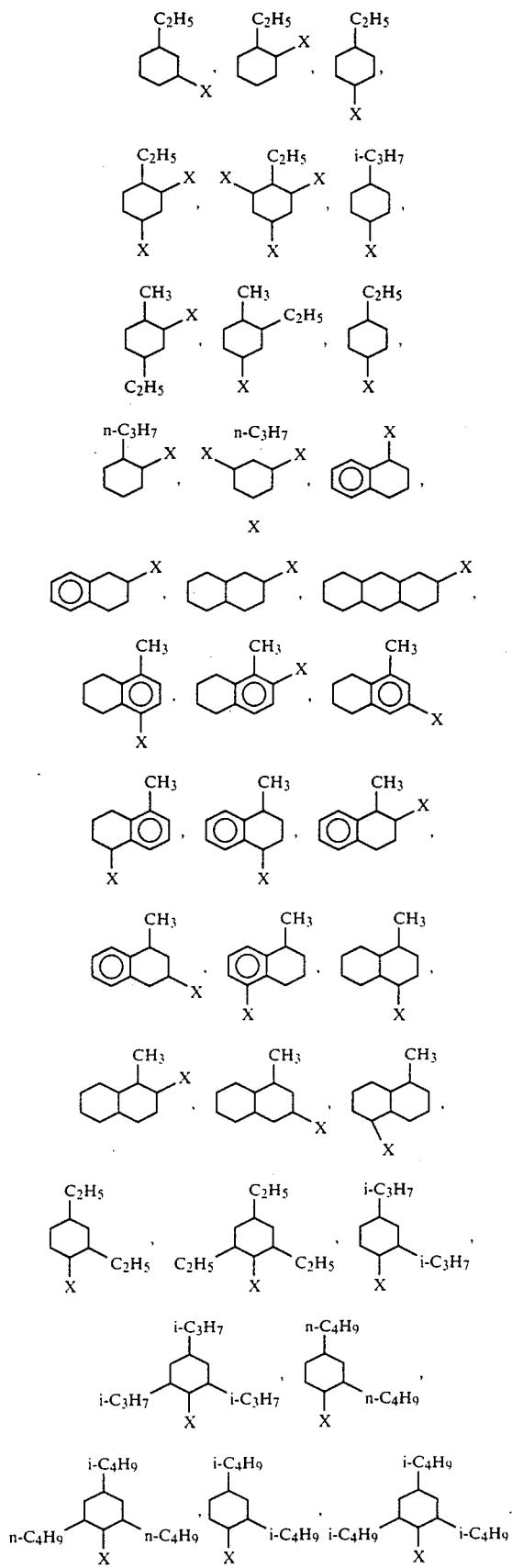

The present inventors found that a partially hydrogenated product having a cyclohexadiene or cyclohexene ring is not substantially formed from the unsubstituted or substituted aromatic hydrocarbon compound having only one benzene ring.

Medium for Transmitting Motive Power

The resulting hydrogenated product of the substituted aromatic hydrocarbon compound has excellent properties as a motive power transmitting medium in various types of machinery. The term "a motive power transmitting medium" used herein means the fluid which transmits or absorbs a motive power.

As mentioned in Japanese Examined (Kokoku) Patent Publications No. 53-36105, No. 46-338, No. 46-339, No. 47-35763, or the like, various materials are used as the motive power transmitting medium in various types of apparatuses, and various properties are required for the motive power transmitting medium, as explained in the above patent publications.

For example, in the case of a medium used in a variable speed motive power transmitting system using a traction drive or traction friction clutch, i.e., a traction oil, properties whereby wear or seizure of the portions of driving and driven elements that are in contact with each other, or whereby the motive power is effectively conveyed, are required.

As an index for a degree of transmittance of a motive power, the following traction coefficient (ft) is used, $$ft = \frac{\text{tranction (friction force)}}{\text{normal load}}$$

and a medium having a high traction coefficient is required. Namely, when a lubricating oil (traction oil) having a high traction coefficient is used, a fuel consumption for a motor vehicle or the like is reduced due to a high traction, or the life of gears is prolonged due to a low normal load.

The hydrogenated product used in the present invention has a high traction coefficient, and thus is an excellent motive power transmitting medium. In the present invention, the motive power transmitting medium may comprise one kind of the hydrogenated product or a mixture of two or more kinds thereof. Of the hydrogenated products used in the present invention, a compound having one of methyl, ethyl and butyl or a cyclohexane ring or a compound having one of methyl, ethyl and butyl on a methylcyclohexane ring is particularly preferable.

Although the motive power transmitting medium according to the present invention may comprise the hydrogenated product alone, it may further comprise another lubricating oil in order to meet demands for various characteristics or functions. As an example of the lubricating oil, there may be mentioned paraffinic oil, naphthenic oil, silicon oil or polyisobutylene etc. Further, the motive power transmitting medium may contain a usually employed additive, such as an anti-oxidizing agent, a dispersing agent, a metal diactivator, a viscosity index improver, an anti-wear agent, a rust preventing agent, a corrosion-resisting agent, an anti-foaming agent, or an agent for adjusting friction.

The characteristics of the motive power transmitting medium according to the present invention will be illustrated in the Examples below.

In the following Examples, the general properties of various hydrogenated products are evaluated by the following methods:

(1) Softening point: JIS (Japanese Industrial Standard) K-5665
(2) Hue: ASTM D 1544-58T; designated by Gardner number (G. No.)
(3) Molecular weight: determined by field desorption ionization mass spectrometry.
(4) Refractive index: determined at 25° C. by Abbe refractometer.
(5) Viscosity: determined at 25° C. by Vismetron manufactured by Toshiba System K. K.

EXAMPLES

The present invention now will be further illustrated by, but is by no means limited to, the following Examples.

REFERENTIAL EXAMPLE 1

A $C_5$-fraction obtained from naphtha cracking was heated at 150° C. for 3 hours to convert cyclopentadiene contained therein to dicyclopentadiene, and crude dicyclopentadiene comprising 20.1% of pentanes and pentenes, 0.5% of benzene, 72.1% of dicyclopentadiene, 4.8% of isoprene-cyclopentadiene co-dimer and 2.5% of cyclopentadiene oligomer was obtained. A metallic autoclave was then charged with 100 parts by weight (1710 g) of the crude dicyclopentadiene and 4 parts by weight of tablet-like palladium hydrogenating catalyst (C31-1A: Toyo C.C.I. K. K.), and hydrogenation was carried out at a reaction temperature of 50° C. under a hydrogen pressure of 10 kg/cm$^2$ for 12 hours while stirring. After filtering off the catalyst and distillation, 90 parts by weight of tricyclo[5.2.1.0$^{2,6}$]deca-3-ene (9,10-dihydrodicyclopentadiene) fraction were obtained. Gas chromatography showed that the composition thereof was as follows:

19.9% pentanes; 70.9% tricyclo[5.2.1.0$^{2,6}$]deca-3-ene; less than 0.1% dicyclopentadiene; 4.5% hydrogenated product of isoprene-cyclo-pentadiene codimer; 2.1% tricyclo[5.2.1.0$^{2,6}$]decane; and 2.6% unidentified components.

REFERENTIAL EXAMPLE 2

To a 500 ml four-necked flask provided with a thermometer, a stirrer, a condenser, and a dropping funnel, were added 195 g (2.5 mole) of benzene and 2 g of pulverized anhydrous aluminium chloride, under a nitrogen atmosphere. Then, while stirring, 94.5 g (0.5 mole) of tricyclo[5.2.1.0$^{2,6}$]deca-3-ene containing fraction (purity of 70.9%; obtained in the above Referential Example 1 and used in the subsequent Examples) was added from a dropping funnel, the whole was heated at 70° C. for 2 hours while stirring and the reaction was terminated by adding methanol. The reaction liquid was then washed until neutralized, and after distillation, 12.5 g of a virtually colorless distillate was obtained at an overhead temperature of 150°–155° C. and a pressure of 5 mmHg. The product was identified as tricyclo[5.2.1.0$^{2,6}$]deca-4-yl benzene by the molecular weight (found: 212, theory:212) and the infrared spectrum as shown in FIG. 1. The refractive index was ($n_D^{25}$) was 1.5558.

REFERENTIAL EXAMPLE 3

To a 500 ml four-necked flask provided with a thermometer, a stirrer, a condenser, and a dropping funnel, were added 400 g (4.35 mole) of toluene and 5 g of pulverized anhydrous aluminium chloride, under a nitrogen atmosphere. Then, while stirring, 126.9 g (0.67 mole) of tricyclo[5.2.1.0$^{2,6}$]deca-3-ene containing fraction (purity of 70.9%) was added from a dropping funnel, the whole was heated at 70° C. for 5 hours with stirring, and the reaction was terminated by adding methanol. The reaction liquid was washed with water, and distillated to obtain 90 g of a colorless distillate having a boiling point of 158°–162° C./5 mmHg. The product was identified as a mixture of 2-, 3- and 4-tricyclo[5.2.1.0$^{2,6}$]deca-4-yl benzenes by the molecular weight (found: 226, theory: 226), the infrared spectrum and by liquid chromatography. The refractive index was ($n_D^{25}$) 1.5582.

REFERENTIAL EXAMPLE 4

To the apparatus used in Referential Example 3, were added 461 g (4.35 mole) of ethylbenzene and 5 g of pulverized anhydrous aluminium chloride, under a nitrogen atmosphere. Then, while stirring, 126.6 g (0.67 mole) of tricyclo[5.2.1.0$^{2,6}$]deca-3-ene containing fraction (purity of 70.9%) was added from a dropping funnel, the whole was heated at 60° C. for 2 hours, and the reaction was terminated by adding methanol. The reaction liquid was washed until neutralized, and after distillation, 115 g of a distillate having a boiling point of 170°–174° C./5 mmHg was obtained. The product was identified as mainly a mixture of 2-, 3- and 4-tricyclo[5.2.1.0$^{2,6}$]deca-4-yl ethylbenzenes by the molecular weight (found: 240; theory: 240) and infrared spectrum.

REFERENTIAL EXAMPLE 5

To the apparatus used in referential Example 2, were added 79.5 g (0.75 mole) of mixed xylene (45% of m-xylene, 51% of ethylbenzene, and 4% of o- and p-xylenes) and 3 g of pulverized anhydrous aluminium chloride, under a nitrogen atmosphere. Then, while stirring, 283.5 g (1.5 mole) of tricyclo[5.2.1.0$^{2,6}$]deca-3-ene containing fraction (purity of 70.9%) was added from a dropping funnel, the whole was heated at 60° C. for 2 hours while stirring, and the reaction was terminated by adding methanol. The reaction liquid was washed until neutralized, and after removing unreacted components at a bottom temperature of 150° C. and a pressure of 20 mmHg, 49 g of a viscous liquid having a Gardner number of 10, a viscosity (at 25° C.) of 10,800 cp, and a refractive index of 1.5482 was obtained. An analysis showed that the product comprised 59% by weight of 1:1 adduct of tricyclo[5.2.1.0$^{2,6}$]deca-3-ene and mixed xylene, 39% by weight of 2:1 adduct of tricyclo[5.2.1.0$^{2,6}$]deca-3-ene and mixed xylene, and 8% by weight of others.

EXAMPLE 1

Figure 2:
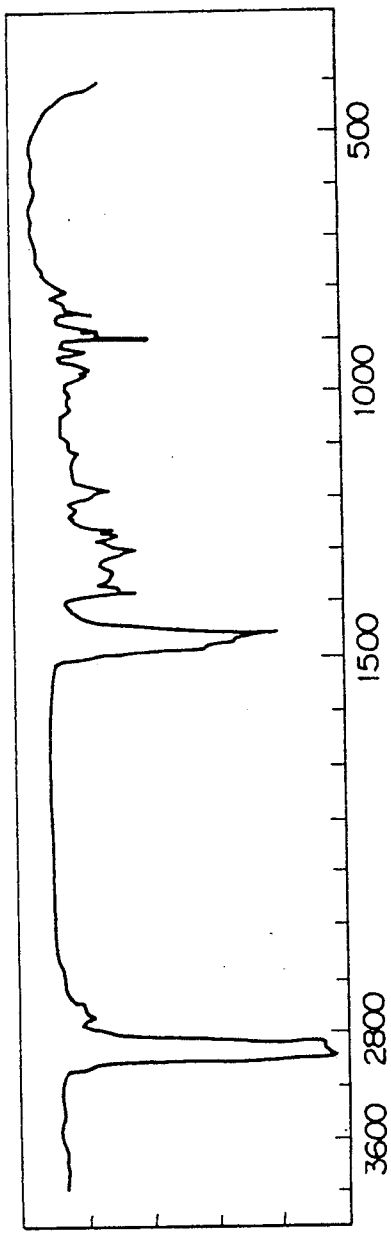

A 500 ml steel autoclave, was charged with 34 g of tricyclo[5.2.1.0$^{2,6}$]deca-4-yl benzene, 118 g of Mitsui hexane (Mitsui Petrochemical Industries Ltd.), and 2.5 g of sulfur resistance nickel catalyst (N-113B, Nikki Kagaku K. K.) as the hydrogenating catalyst. The hydrogenation was carried out at a reaction temperature of 200° C. and under a reaction pressure of 40 kg/cm$^2$G for 5 hours, and after cooling, was reduced by depressurizing and replacing with nitrogen, the catalyst was filtered off, and the filtrate was distillated to obtain 33 g of a colorless distillate at an overhead temperature of 144°–150° C. and a pressure of 7 mmHg. The product was identified as tricyclo[5.2.1.0$^{2,6}$]deca-4-yl cyclohexane, by the molecular weight (found: 218, theory: 218) and infrared spectrum as shown in FIG. 2. The refractive index ($n_D^{25}$) was 1.5110.

EXAMPLE 2

According to the procedure used in Example 1, the mixture of 2-, 3- and 4-tricyclo[5.2.1.0$^{2,6}$]deca-4-yl toluenes obtained in Referential Example 3 was hydrogenated under the condition listed in Table 1 below. After the hydrogenation was completed, the catalyst was filtered off, and the filtrate was distillated at an overhead temperature of 154°-158° C. under a pressure of 7 mmHg to obtain 78 g of a colorless distillate. The product was identified as a mixture of 2-, 3- and 4-tricyclo[5.2.1.0$^{2,6}$]deca-4-yl methylcyclohexanes by the molecular weight (found: 232, theory: 232), etc. The refractive index was (n$_D^{25}$) was 1.5080.

EXAMPLE 3

According to the procedure used in Example 1, the mixture of 2-, 3- and 4-tricyclo[5.2.1.0$^{2,6}$]deca-4-yl ethylbenzenes obtained in Referential Example 4 was hydrogenated under the condition listed in Table 1 below. After the hydrogenation was completed, the catalyst was filtered off, and the filtrate was distillated at an overhead temperature of 163°-168° C. under a pressure of 7 mmHg to obtain 98 g of a colorless distillate. The product was identified as a mixture of 2-, 3- and 4-tricyclo[5.2.1.0$^{2,6}$]deca-4-yl ethylcyclohexanes by the molecular weight (found: 246, theory: 246), etc.

EXAMPLE 4

According to the procedure used in Example 1, the mixture obtained in Referential Example 5 (comprising 59% by weight of 1:1 adduct of tricyclo[5.2.1.0$^{2,6}$]deca-3-ene and mixed xylene, 33% by weight of 2:1 adduct of tricyclo[5.2.1.0$^{2,6}$]deca-3-ene and mixed xylene, and 8% by weight of others) was hydrogenated under the condition listed in Table 1 below. After the hydrogenation was completed, the catalyst was filtered off and the solvent was removed from the filtrate at a temperature of 150° C. under a pressure of 20 mmHg to obtain 39 g of a viscous liquid having a viscosity (at 25° C.) of 10,600 cp and a refractive index (n$_D^{25}$) of 1.5028. An analysis showed that the product comprised 59% by weight of the hydrogenated product of a 1:1 adduct of tricyclo[5.2.1.0$^{2,6}$]deca-3-ene and mixed xylene, 33% by weight of hydrogenated product of a 2:1 adduct of tricyclo[5.2.1.0$^{2,6}$]deca-3-ene and mixed xylene, and 8% by weight of others.

TABLE 1

|  | Example 1 | Example 2 | Example 3 | Example 4 |
| --- | --- | --- | --- | --- |
| Hydrogenation |  |  |  |  |
| Substituted aromatic hydrocarbon compound prepared in | Referential Example 2 | Referential Example 3 | Referential Example 4 | Referential Example 5 |
| Amount of the above compound used (g) | 34 | 80 | 100 | 40 |
| Solvent (g) | Mitsui Hexane | Mitsui Hexane | Mitsui Hexane | Mitsui Hexane |
| Amount of solvent uxed (g) | 118 | 195 | 200 | 139 |
| Catalyst |  |  |  |  |
| Kind | Sulfur resistance nickel | Sulfur resistance nickel | Sulfur resistance nickel | Sulfur resistance nickel |
| Amount | 2.5 | 5.8 | 7.3 | 2.9 |
| Reaction temperature (°C.) | 200 | 200 | 200 | 200 |
| Reaction time (HR) | 5 | 5 | 5 | 5 |
| Reaction pressure (kg/cm$^2$) | 40 | 40 | 40 | 40 |
| Yield of hydrogenated product (g) | 33 | 78 | 98 | 39 |

EXAMPLES 5 TO 8 AND COMPARATIVE EXAMPLES 1 TO 3

The properties (boiling point, viscosity, pour point, and traction coefficient) of the hydrogenated products of the substituted aromatic hydrocarbon compounds obtained in Examples 1 to 4 are listed in Table 2, as Examples 5 to 8, respectively, and as Comparative Examples, the properties of 2-methyl-2,4dicyclohexylpentane obtained by hydrogenating a linear dimer of α-methylstyrene [Comparative Example 1], hydrogenated polybutene (Polybutene OH manufactured by Idemitsu Petrochemical Industries Ltd.) [Comparative Example 2], and naphthene base mineral oil (Shellflex 371JY manufactured by Shell Chemical) [Comparative Example 3] are shown.

The properties were evaluated by the following methods:

Viscosity: E-type viscometer (Tokyo Keiki K. K.)
Pour point: JIS K-2269
Fraction coefficient (ft): determined by inkometer (B45 type manufactured by Toyo Seiki K. K.) at 1,200 rpm and the following equation: ft=Ft/Pn wherein Ft is traction and Pn is a normal load (2500 g).

TABLE 2

|  |  | Example 5 | Example 6 | Example 7 | Example 8 | Comparative Example 1 | Comparative Example 2 | Comparative Example 3 |
| --- | --- | --- | --- | --- | --- | --- | --- | --- |
| Boiling point (°C./mm Hg) |  | 144–150/7 | 154–158/7 | 163–168/7 | — | 130–150/2–3 | — | — |
| Viscosity (cp/20° C.) |  | 40 | 45 | 87 | 10.470 | 59 | 54 | 280 |
| Pour point (°C.) |  | −35 | −35 | −32.5 | −20 | −30 | −50 | −20 |
| Traction coefficient | 23° C. | 0.095 | 0.094 | 0.092 | 0.151 | 0.081 | 0.070 | 0.051 |
| (ft) | 33° C. | 0.084 | 0.083 | 0.082 | 0.127 | 0.073 | 0.064 | 0.034 |

It is apparent from Table 2 that the hydrogenated product of the present invention is very useful as a motive power transmitting medium, particularly as a traction oil.

Although the present invention has been described with reference to specific embodiments, various changes and modifications obvious to those skilled in the art are deemed to be within the spirit, scope and concept of the invention.

We claim:

1. A process for transmitting motive power, comprising:

providing a motive power transmission medium comprising a hydrogenated product of an aromatic hydrocarbon compound in which at least one hydrogen atom on the aromatic nucleus is substituted by a tricyclo[5.2.1.0$^{2,6}$]deca-3-yl or tricyclo[5.2.1.0$^{2,6}$]deca-4-yl group which is substituted with one or more lower alkyl group; and transmitting motive power through said motive power transmission medium.

2. The process according to claim 1, wherein the aromatic hydrocarbon compound has 6 to 18 carbon atoms.

3. The process according to claim 1 wherein the aromatic hydrocarbon compound further carries at least one saturated substituent other than the tricyclo[5.2.1.0$^{2,6}$]deca-3-yl or tricyclo[5.2.1.0$^{2,6}$]deca-4-yl.

4. The process according to claim 3 wherein said at least one saturated substituent is a straight-chain or branched-chain lower alkyl group.

5. The process according to claim 1, wherein said hydrogenated product is a mixture of the products prepared by hydrogenating an aromatic hydrocarbon compound in which at least one hydrogen atom on the aromatic nucleus is substituted by a tricyclo[5.2.1.0$^{2,6}$]deca-3-yl or tricyclo]5.2.1.0$^{2,6}$]deca-4-yl group which is unsubstituted or substituted with one or more lower alkyl group.

* * * * *